US011931969B2

(12) United States Patent
Hudson et al.

(10) Patent No.: US 11,931,969 B2
(45) Date of Patent: Mar. 19, 2024

(54) ADDITIVE MANUFACTURING BASED ON FLUID-FLUID INTERFACE

(71) Applicant: Carnegie Mellon University, Pittsburgh, PA (US)

(72) Inventors: Andrew Hudson, Pittsburgh, PA (US); Thomas Hinton, Pittsburgh, PA (US); Adam Feinberg, Pittsburgh, PA (US); Andrew Lee, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 281 days.

(21) Appl. No.: 16/603,173

(22) PCT Filed: Apr. 6, 2018

(86) PCT No.: PCT/US2018/026604
§ 371 (c)(1),
(2) Date: Oct. 4, 2019

(87) PCT Pub. No.: WO2018/187780
PCT Pub. Date: Oct. 11, 2018

(65) Prior Publication Data
US 2020/0189202 A1 Jun. 18, 2020

Related U.S. Application Data

(60) Provisional application No. 62/606,581, filed on Sep. 28, 2017, provisional application No. 62/601,995, filed on Apr. 6, 2017.

(51) Int. Cl.
*B29C 64/40* (2017.01)
*A61L 27/20* (2006.01)
(Continued)

(52) U.S. Cl.
CPC .............. *B29C 64/40* (2017.08); *A61L 27/20* (2013.01); *A61L 27/222* (2013.01); *A61L 27/24* (2013.01);
(Continued)

(58) Field of Classification Search
CPC ..... B29C 64/40; B29C 64/124; B29C 64/209; B29C 64/336; B29C 64/106;
(Continued)

(56) References Cited

U.S. PATENT DOCUMENTS

| 8,470,231 B1 | 6/2013 | Dikovsky et al. |
| 2008/0111282 A1 | 5/2008 | Xie et al. |

(Continued)

FOREIGN PATENT DOCUMENTS

| CN | 101032430 | 9/2007 |
| CN | 104887346 | 9/2015 |

(Continued)

OTHER PUBLICATIONS

Lee et al. On-Demand Three-Dimensional Freeform Fabrication of Multi-Layered Hydrogel Scaffold with Fluidic Channels. Biotechnology and Bioengineering, vol. 105, No. 6, (Year: Apr. 15, 2010).*

(Continued)

*Primary Examiner* — Yashita Sharma
(74) *Attorney, Agent, or Firm* — Fish & Richardson P.C.

(57) ABSTRACT

This document describes systems and method of embedded printing for additive manufacturing. A print material is printed into a support material. The print material and the support material each have a fluid phase and a solid phase. The print material transitions from the fluid phase to the solid phase based on a fluid-fluid interaction with the support material. One or more parameters of the support material can be adjusted to cause a diffusion rate of the print material into the support material during the fluid-fluid (Continued)

interaction to be less than a threshold value. Multiple print materials can be printed into the support material simultaneously.

9 Claims, 13 Drawing Sheets

(51) Int. Cl.
| | |
|---|---|
| A61L 27/22 | (2006.01) |
| A61L 27/24 | (2006.01) |
| A61L 27/52 | (2006.01) |
| A61L 27/56 | (2006.01) |
| B29C 64/106 | (2017.01) |
| B29C 64/165 | (2017.01) |
| B33Y 10/00 | (2015.01) |
| B33Y 30/00 | (2015.01) |
| B33Y 70/00 | (2020.01) |

(52) U.S. Cl.
CPC .............. *A61L 27/52* (2013.01); *A61L 27/56* (2013.01); *B29C 64/106* (2017.08); *B29C 64/165* (2017.08); *B33Y 10/00* (2014.12); *B33Y 30/00* (2014.12); *B33Y 70/00* (2014.12)

(58) Field of Classification Search
CPC ...... B29C 64/165; A61L 27/20; A61L 27/222; A61L 27/24; A61L 27/52; A61L 27/56; A61L 27/38; B33Y 40/00; B33Y 10/00; B33Y 30/00; B33Y 70/00; C08L 5/04
See application file for complete search history.

(56) References Cited

U.S. PATENT DOCUMENTS

| | | |
|---|---|---|
| 2010/0196432 A1 | 8/2010 | Feinberg et al. |
| 2013/0046134 A1 | 2/2013 | Parker et al. |
| 2016/0167312 A1* | 6/2016 | Feinberg .................. A61L 27/24 264/239 |
| 2016/0279868 A1 | 9/2016 | Burdick et al. |
| 2016/0287756 A1 | 10/2016 | Lewis et al. |

FOREIGN PATENT DOCUMENTS

| | | |
|---|---|---|
| EP | 2854883 | 4/2015 |
| WO | WO1996/14095 | 5/1996 |
| WO | WO2016090286 | 6/2016 |
| WO | WO2016172699 | 10/2016 |

OTHER PUBLICATIONS

Sigma-Aldrich Gelatin Product Information Sheet. (Year: 2021).*
Boland, et al. "Application Of Inkjet Printing To Tissue Engineering". Biotechnology Journal, vol. 1, No. 9, pp. 910-917. (Year: 2006).*
Nixon, et al. "Gelatin coacervate microcapsules containing sulphamerazine: Their preparation and the in vitro release of the drug". Journal of Pharm. Pharmac., vol. 20, pp. 528-538. (Year: 1968).*
EP Search Report in European Appln. No. 18781195.5, dated Mar. 25, 2020, 8 pages.
Hinton, "Rapid Prototyping Tissue Models of Mammary Duct Epithelium," for Doctor of Philosophy in Biomedical Engineering, Carnegie Mellon University, Pittsburgh, PA, Apr. 2017, 54 pages.
PCT International Search Report and Written Opinion issued in International Application No. PCT/US18/26604 dated Jun. 29, 2018, 34 pages.
PCT International Preliminary Report on Patentability in International Application No. PCT/US2018/026604, dated Oct. 8, 2019, 9 pages.
Extended European Search Report in European Appln. No. 22200596.9, dated Feb. 2, 2023, 9 pages.
endmemo.com [online], "NaHCO3," 2020, retrieved on Jul. 1, 2022, retrieved from URL <http://www.endmemo.com/chem/massmolarconcentration.php?1+g%2FL&s=mol%2FL>, 4 pages.
Guvendiren et al., "Shear-thinning hydrogels for biomedical applications," Soft Matter, Jan. 2012, 8(2):260-272.

* cited by examiner

|  |  | Direct Write | Carbopol Bath | Self Heal Bath | FRESH |
|---|---|---|---|---|---|
|  | Overhangs | no | yes | yes | yes |
|  | Speed (mm/s) | 5 | 10 | 10 | 80 |
|  | Medium | air | carbopol | gel | gelatin slurry |
|  | Isotonic Chemistry | dry | no | yes | yes |
|  | Damageless | yes | no | no | yes |
| Fluid Inks | ECM Gels — Collagen | no | yes | yes | yes |
|  | Matrigel | no | yes | yes | yes |
|  | Fibrin | no | yes | yes | yes |
|  | Cells | yes | yes | yes | yes |
|  | Thixotropic/Yield-Stress Fluids — Slurries | yes | yes | yes | yes |
|  | Resins | yes | yes | yes | yes |
|  | Alginate-CaSO4 | yes | yes | yes | yes |
|  | Poloxamer Gels | yes | yes | yes | yes |
|  | Ionic Gels — Alginate | no | no | yes | yes |
|  | Cellulose | no | no | yes | yes |
|  | Photopolymer — Acrylates | yes | yes | yes | yes |

FIG. 9

ADDITIVE MANUFACTURING BASED ON FLUID-FLUID INTERFACE

CLAIM OF PRIORITY

This application is a 35 U.S.C. § 371 National Stage Application of PCT/US2018/026604, filed Apr. 6, 2018, which, in turn, claims the benefit of priority under 35 U.S.C. § 119(e) to U.S. patent Application Ser. No. 62/601,995, filed on Apr. 6, 2017, and Application Ser. No. 62/606,581, filed Sep. 28, 2017, the entire contents of each of which are hereby incorporated by reference.

GOVERNMENT SUPPORT CLAUSE

This invention was made with government support under the National Institutes of Health No. HL117750. The government has certain rights in this invention.

TECHNICAL FIELD

This application relates to additive manufacturing, specifically embedded printing.

BACKGROUND

Additive manufacturing can be used to create three dimensional objects or structures. A material can be printed into a support scaffolding that temporarily supports the structure during assembly. When assembly is completed, the support scaffold is removed.

SUMMARY

This application describes a support material and a printed material that are used for additive manufacturing. A process for additively manufacturing fluids called Freeform Reversible Embedding of Suspended Hydrogels (FRESH) includes embedding a fluid material (e.g., alginate, collagen, fibrin, etc.) into a fugitive support material (e.g., comprising a slurry) comprising a solid phase and a fluid phase.

The support material includes a solid and fluid phase. In some implementations, the solid phase includes gelatin particles that impart a Bingham Plastic behavior to the support material, which allows for deposition and support of gelling fluids. The fluid phase suspends the gelatin particles, and its volume and composition has previously been shown to influence the rheological properties of the support material. The composition of the fluid phase can be used to control the gelling behavior of the embedded fluid inks. Previously, alginate has been printed into a support material with a fluid phase containing calcium cations to facilitate alginate gelation. Expanding beyond the initial use of alginate, physical and chemical modifications can be made to the fluid phase to tune the gelation of other fluid inks, most notably collagen. The fluid phase of the print material interacts with the fluid phase of the support material, forming a fluid-fluid interface. The fluid-fluid interface between the support material and embedded hydrogel inks to tune the gelling behavior of the inks allows the use of FRESH to be expanded to both organic polymers such as fibrin, collagen and matrigel as well as synthetic polymers, including epoxies, rubbers and cements.

The system described below includes a support material configured to transition from a first solid phase to a first fluid phase in response to experiencing a stress; and a print material embedded in the support material, the print material configured to transition from a second fluid phase to a second solid phase in the support material by a fluid-fluid interaction between the first fluid phase of the support material and the second fluid phase of the print material.

In some implementations, the support material is basic and the print material is acidic, and where transition of the support material comprises neutralization of the print material during the fluid-fluid interaction of the print material and the support material. In some implementations, the print material comprises at least one of collagen, gelatin, and alginate. In some implementations, the print material comprises a strand including a diameter between about 60-80 micrometers. In some implementations, the print material is a first print material, and where the system comprises a second print material that forms a mesh that encases the first print material, the mesh configured to support a geometry of the first print material when the support material is removed from the first print material. In some implementations, the first print material comprises collagen, where the second print material comprises alginate, and where the support material comprises calcium. In some implementations, the print material is configured to allow cell infiltration into voids formed by removing the gel particles from the print material. The support material comprises a coacervate slurry.

In some implementations, the support material comprises gel particles, the gel particles formed by tuning a salt concentration of the support material, where the gel particles are mixed with the print material.

This processes described in this application include moving an injector inside a support material configured to transition between a first solid phase and a first fluid phase, causing, by the injector, a portion of the support material to change from the first solid phase to the first fluid phase, injecting a print material into the support material, transitioning the print material from a second fluid phase to a second solid phase in the support material based on a fluid-fluid interaction between the first fluid phase of the support material and the second fluid phase of the print material, and removing the support material from the print material.

In some implementations, the process includes acidifying the print material and alkalizing the support material, where transition of the support material comprises neutralization of the print material during the fluid-fluid interaction of the print material and the support material.

In some implementations, the process includes controlling a nanostructure of print material in the second solid phase by controlling a pH of the support material.

In some implementations, the print material comprises at least one of collagen, gelatin, and alginate. In some implementations, the process includes selecting a parameter of the support material; and adjusting a value of the parameter of the support material based on a type of the print material, the value of the parameter being configured to increase a rate of transition of the print material from the second fluid phase to the second solid phase during the fluid-fluid interaction, relative to a rate of transition of the print material from the second fluid phase to the second solid phase during the fluid-fluid interaction when the value of the parameter is not adjusted. In some implementations, the parameter of the support material comprises one of a fluid-phase composition, pH, an ionic strength, a buffering capacity, and an enzymatic activity.

In some implementations, the process includes selecting a parameter of the support material; and adjusting a value of the parameter of the support material based on a type of the print material, the value of the parameter being configured to decrease a diffusion rate of the print material into the support material during the fluid-fluid interaction, relative to a diffusion rate of the print material into the support material during the fluid-fluid interaction when the value of the parameter is not adjusted. In some implementations, the parameter of the support material includes one of a fluid-phase composition, pH, an ionic strength, a buffering capacity, and an enzymatic activity.

In some implementations, the process includes mixing the support material into the print material during the injecting, where removing the support material causes one or more voids in the second solid phase of the print material. In some implementations, mixing the support material into the print material comprises controlling a salt concentration of the support material to cause gel particles to form in the support material, where the gel particles mix with the print material during the fluid-fluid interaction.

In some implementations, the second solid phase of the print material comprises collagen strands having an average diameter of between about 60-80 micrometers. In some implementations, the print material comprises a first print material, the method including: modifying the support material based on a type of the first print material and a type of a second print material; and injecting the first print material and the second print material into the support material. In some implementations, the first print material comprises collagen, where the second print material comprises alginate, where the support material comprises calcium cations.

In some implementations, a printing system includes an injector, a coacervate gelatin support bath including a salt concentration above 20 g/L NaCl and gum arabic, the gelatin support bath being above a pH of 8 and configured to transition from a first solid phase to a first fluid phase in response to experiencing a stress above a yield stress threshold; and a collagen and an alginate configured for injection into the support material by the injector, where the collagen and the alginate each have a pH below 6, where the collagen and the alginate are each configured for gelation in the coacervate gelatin support bath, and where the gelatin and the alginate each diffuse less than 10% into the support bath during gelation.

The details of one or more embodiments are set forth in the accompanying drawings and the description below. Other features, objects, and advantages are apparent from the description and drawings, and from the claims.

DESCRIPTION OF DRAWINGS

FIG. 9 shows a comparison between additive manufacturing techniques.

Like reference symbols in the various drawings indicate like elements.

DETAILED DESCRIPTION

Figure 1:
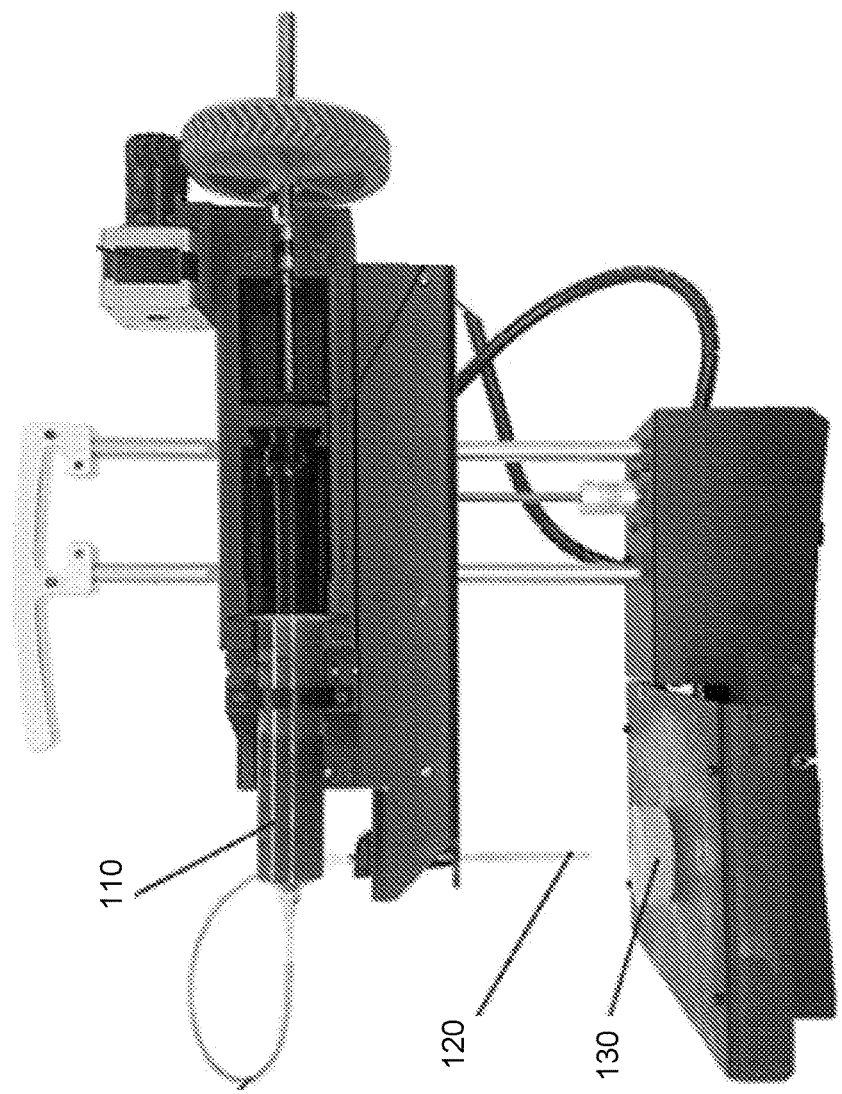
FIG. 1 shows a printing system.

FIG. 1 shows a printing system 100. The printing system 100 is configured to print a material 110 (e.g., collagen, fibrin, matrigel, epoxy, rubber, cement, etc.) embedded into a support material 130 (e.g., alginate, gelatin, cellulose, etc.), such as through an injector 120. The printed material 110 and the support material 130 each have a solid phase and a fluid phase. The printed material 110 is printed in a fluid phase and transitions to a solid phase upon interaction with the support material 130. The support material 130 transitions from a solid phase to a fluid phase when stress above a yield stress (e.g., a critical shear stress) is exerted on the support material. For example, motion of the injector 120 through the support material 130 can cause stress on the support material above a yield stress threshold. This can cause the support material 130 to transition to a fluid phase around the injector 120.

The support material 130 forms a scaffold to support the material 110 while printing is conducted and while the printed material hardens from a fluid phase to a solid phase (e.g., while gelation occurs). When the viscosity and yield stress of the support material 130 are similar to the printed material (also referred to as an ink), the printing system 100 can print with greater precision than when the viscosity and yield stress of the support material 130 do not match or are not similar to those of the support material. Further, a support material 130 that forms a slurry with smaller particles facilitates high-fidelity printing of a structure in the support material by the printing system 100.

In some implementations, the support material (also referred to as a support bath, support medium, etc.) exhibits at least some of the properties of a Bingham plastic. For example, the support material exhibits the properties of a solid material when the support material is not experiencing a stress (e.g., a shear stress) that is above a yield stress value. A least a portion of the support material 130 behaves like a viscous liquid when the portion of the support material experiences a stress (e.g., a shear stress) above the yield stress value. In some implementations, a printer injector 120 applies the stress to the support material as it moves through the support material. This enables the printer head to inject printed material 110 (also referred to as ink) into the support material 130, which supports the ink in place until the structure has been formed. The ink 110 may include tissues such as collagen, fibrin, epoxy, cement, rubber, alginate, or other materials, such as materials that undergo gelation after being injected into the support material 130. The support material 130 supports the ink until gelation is completed. The support material can then be removed (e.g., melted away).

The transition of the printed material 110 from the fluid phase to the solid phase, and how the transition occurs, affects a quality of a structure that is being printed. Controlling the transition is useful for increasing print fidelity. The transition of the printed material 110 can be controlled by controlling a fluid-fluid interaction between the printed material and the support material 130. The fluid-fluid interaction is an interaction between the fluid phase of the print material and the fluid phase of the support material. The fluid-fluid interaction occurs when the print material is inserted (e.g., injected) into the support material. The support material transitions from a solid phase to a fluid phase during the insertion and at the point of insertion of the print material. The print material, printed as a fluid, meets the support material at a fluid-fluid interface (e.g., where the print material and the support material meet and interact). For example, the support material causes gelation of the print material or otherwise causes a transition of the print material from a fluid to a solid. The fluid-fluid interaction can be controlled based on selection of various parameters of the support material 130 and the printed material 110, as described in detail below.

The fluid phase of the support material 130 can be specifically engineered to predictably control collagen type I embedding and gelation within the support material. Controlling the fluid phase of the support material enables complex print geometries with high fidelity. Collagen type I is soluble in acidic conditions. Such solubility is reversed when the pH and temperature of a collagen type I solution is driven to a neutral pH and 37° C. Neutralization of the acidic collagen I solution is achieved by replacing the fluid phase of the support material with a high pH solution. Neutralization means causing the print material to be made approximately neutral from an acidic or basic state, such that the pH of the material is approximately 7 (e.g., between 6-8). Briefly, the support material is centrifuged to separate the solid and the fluid phase. The supernatant is removed and replaced with a NaOH solution that is thoroughly mixed with the solid phase. These steps are repeated until the desired pH is achieved. Printing into this high pH support material results in high fidelity, repeatable embedding of single 80 µm strand of polymerized collagen type I, as shown in FIGS. 2-6 and as described below.

Support material pH is only one of many fluid phase parameters that can be modified in this way to control the fluid to solid transition of gelling materials. Fluid-phase composition, chemistry, ionic strength, buffering capacity, enzymatic activity are some of the variables that can be easily fine-tuned within the support material and tailored specifically for various inks. With this method, multiple inks can also be printed together into a single support material 130 bath that has been modified to facilitate gelation for each ink. For example, separate collagen and alginate inks can be printed into a single high pH support material containing calcium cations to construct a single multi-material print. This method of engineering the fluid-fluid interface to control gelation is only limited in the chemical and physical effects the altered fluid phase might have on the solid gelatin particles. Gelatin hydrolysis can occur at extreme pHs, and presence of ions can influence gelatin particle density, size, and morphology. The ease with which the fluid phase of the support material 130 can be modified, and the large range of factors that can be tuned within a fluid phase, enables changes in rheology of the support material to be addressed.

In some implementations, the support material is a coacervate slurry such as described in Application Ser. No. 62/601,949, filed on Apr. 5, 2018, and Application Ser. No. 62/601,578, filed on Sep. 28, 2017, each of which is incorporated in its entirety herein by reference. The coacervate slurry includes gel microparticles. The geometry of the particles, including the size and the shape of the particles, can be controlled based on the process by which the coacervate slurry is produced and the material used for the coacervate. The particles can be between 0.5 micrometers and 60 micrometers in diameter, with a variance of less than 35%. The particles can be monodisperse in the slurry. The gel particles can mix with the printed material (e.g., collagen) during printing process. When the slurry is removed (e.g., melted away), voids are left in the printed collagen. The voids are thus of substantially uniform size and distribution throughout the printed material. The semi-porous printed material is especially useful for in-vivo applications. The voids of the printed material can facilitate cell infiltration for in-vivo applications of printed structures. The number of voids and distribution of voids can be controlled by controlling gelation of the printed material as described in this application.

Figure 2:
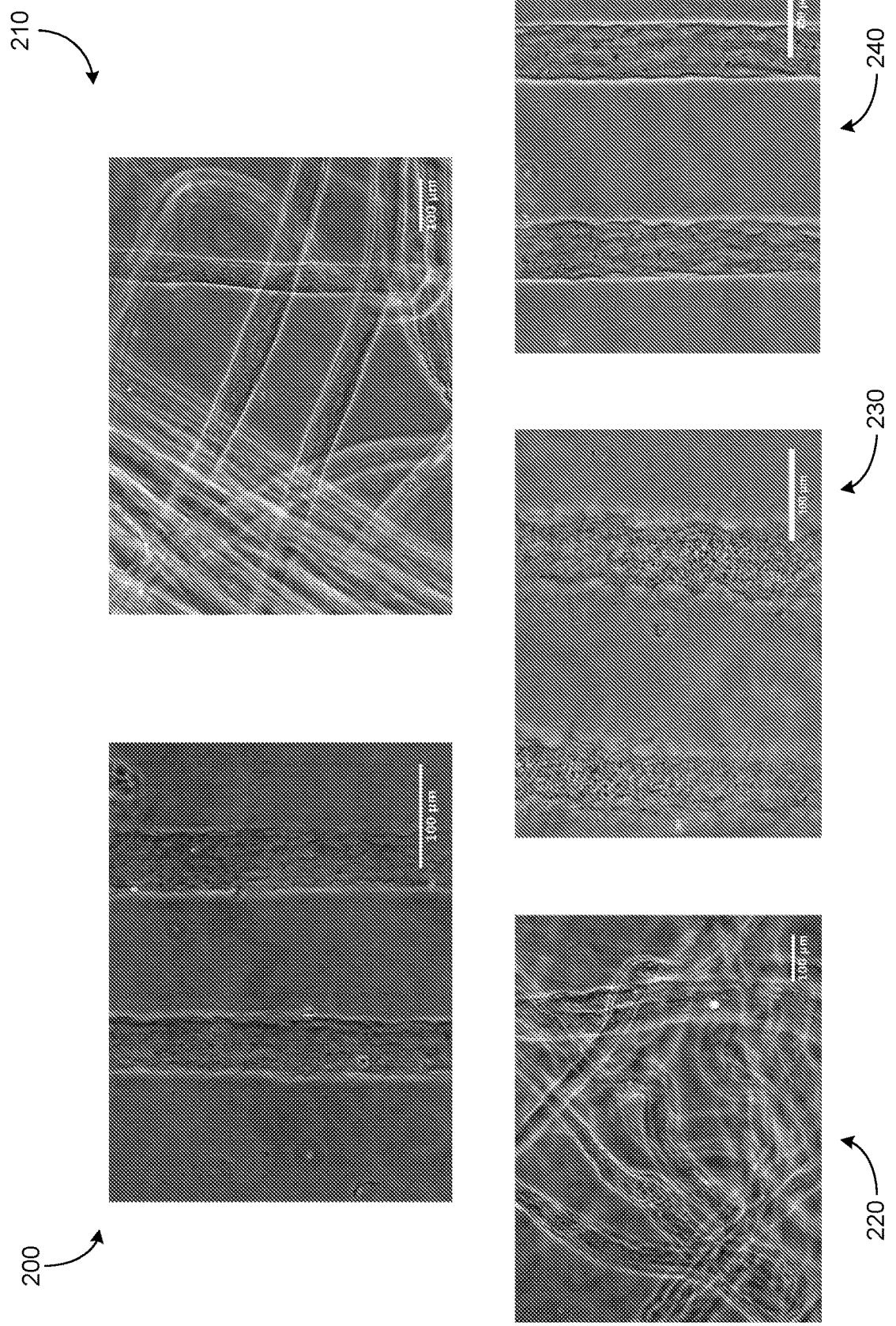
FIGS. 2-7 each show representations of printed strands in example support materials.

FIG. 2 shows examples of strands that have been printed into support materials with different parameters. Strands 200, 210 are printed into a Hyclone 10× phosphate buffered saline (PBS) based support material. Strands printed into 10× PBS are smooth and consistent in diameter, and have relatively low strand-to-strand fusion compared to stands printed in other support materials described below. Strands 220 are printed into a support material with 80 g/L NaCl, which is an elevated salt concentration relative to a baseline support material salt concentration. High salt concentration (80 g/L) alone is sufficient for inducing collagen assembly, most likely via salting-out. Strands 230 are printed into a support material with a 10× phosphate buffer. Strands 240 are printed into a support material with the 10× phosphate buffer and elevated NaCl concentrations. An elevated phosphate buffer concentration creates strands that are not as smooth as when salt is added back into the phosphate buffer.

Figure 3:
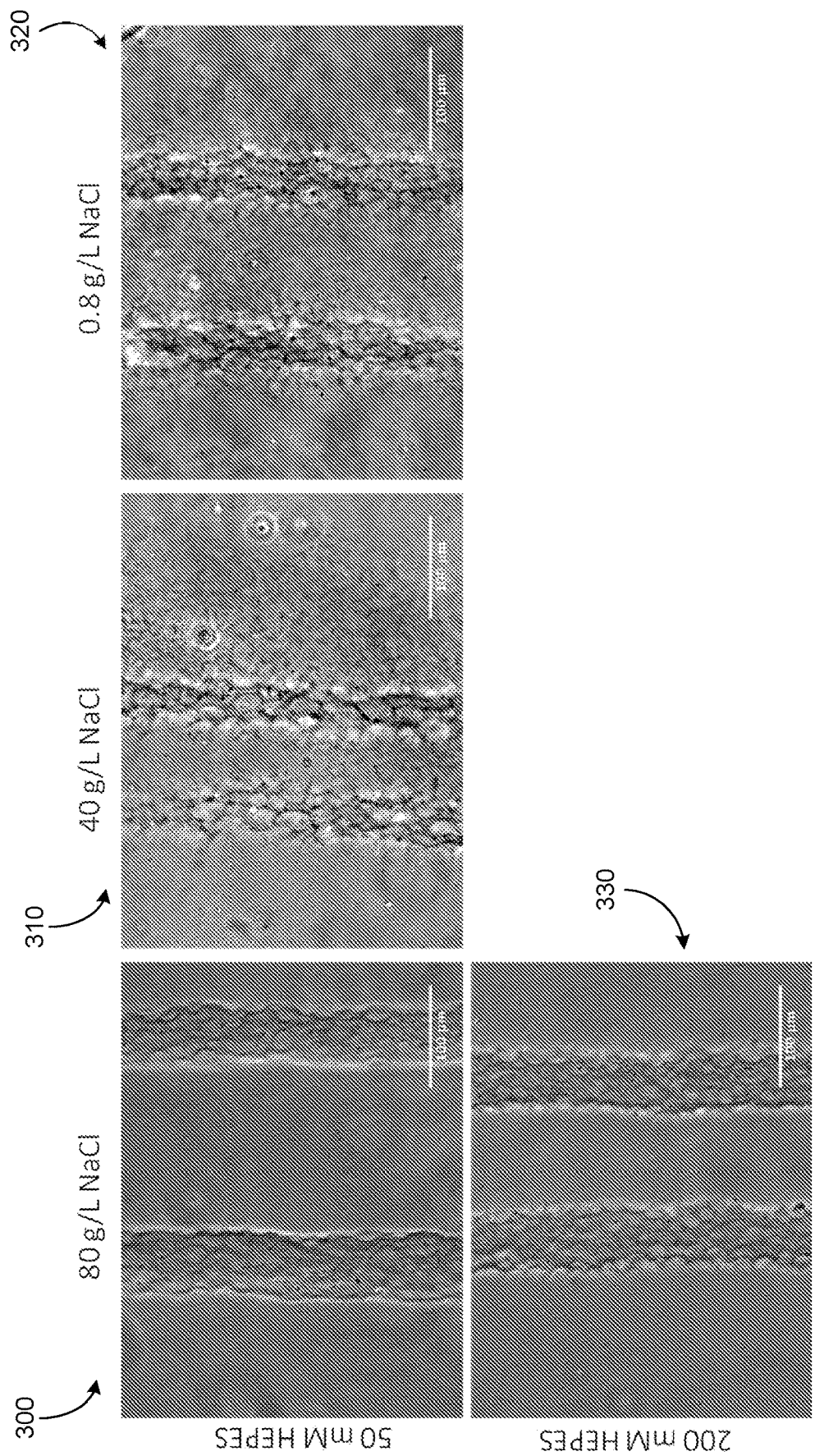

FIG. 3 shows examples of strands that have been printed into support materials with different parameters. Strands 300 are printed into 50 mM HEPES buffer solution that also includes a salt concentration of 80 g/L of NaCl. Strands 310 are printed into 50 mM HEPES buffer solution that also includes a salt concentration of 40 g/L of NaCl. Strands 320 are printed into 50 mM HEPES buffer solution that also includes a salt concentration of 0.80 g/L of NaCl. Strands 330 are printed into 200 mM HEPES buffer solution that also includes a salt concentration of 80 g/L of NaCl. A high NaCl concentration in the support material facilitates a "smooth" printed collagen strand. A 50 mM HEPES solution of the support material sufficient for formation of these strands. A typical cell culture media is 15-20 mM HEPES. In each image showing strands 300, 310, 320, 330, there is some diffusion of the printed material into the support material, but this is limited to less than 10% of the printed material. In some implementations, the diffusion is less than 1% of the printed material. These support materials are especially useful for dual alginate and collagen printing, because the ability to substitute phosphate buffer with a HEPES buffer allows the addition of calcium ions.

Figure 4:
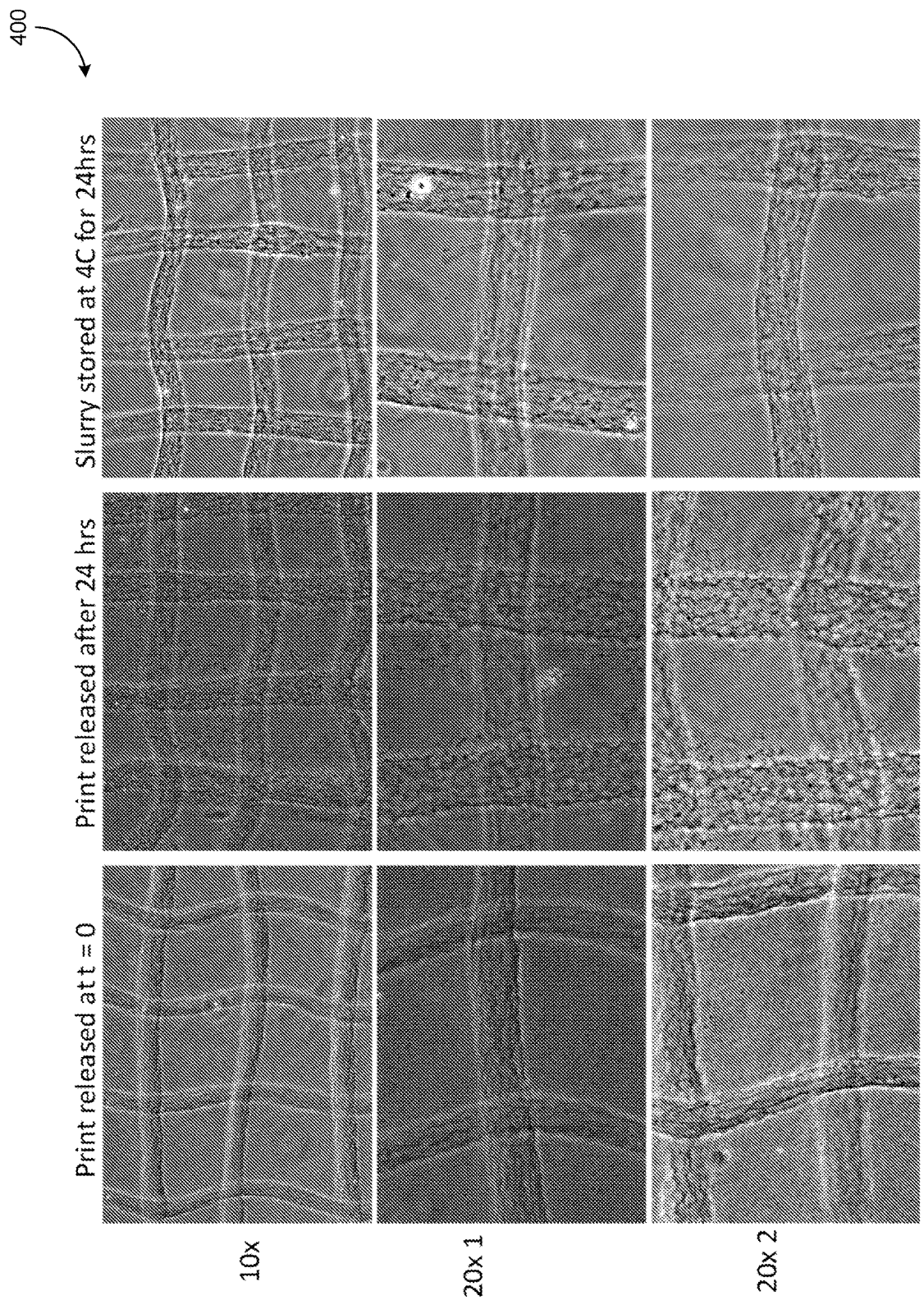

FIG. 4 shows images 400 of printed strands at different buffer strengths and after different amounts of elapsed time since printing. The top row shows strands printed in a support material including a solution with 10× PBS. The middle row shows strands printed in a support material including a solution with 20×1% buffer. The bottom row shows strands printed in a support material including a solution with 20×2% buffer. The left column shows images of the strands immediately after printing into the support material. The middle column shows strands 24 hours after being printed into the support material. The right column shows strands 24 hours after being printed into the support material and being stored at 4° C. For each of the strands, the printed material includes 2% Fisher Gel B. A 0.25% F127 1% gum arabic is included, and the pH is 6. The wash solution includes 50 mM HEPES, 0.16% $CaCl_2$, 80 g/L NaCl. Centrifugation was at 2000 g for 5 minutes.

Figure 5A:
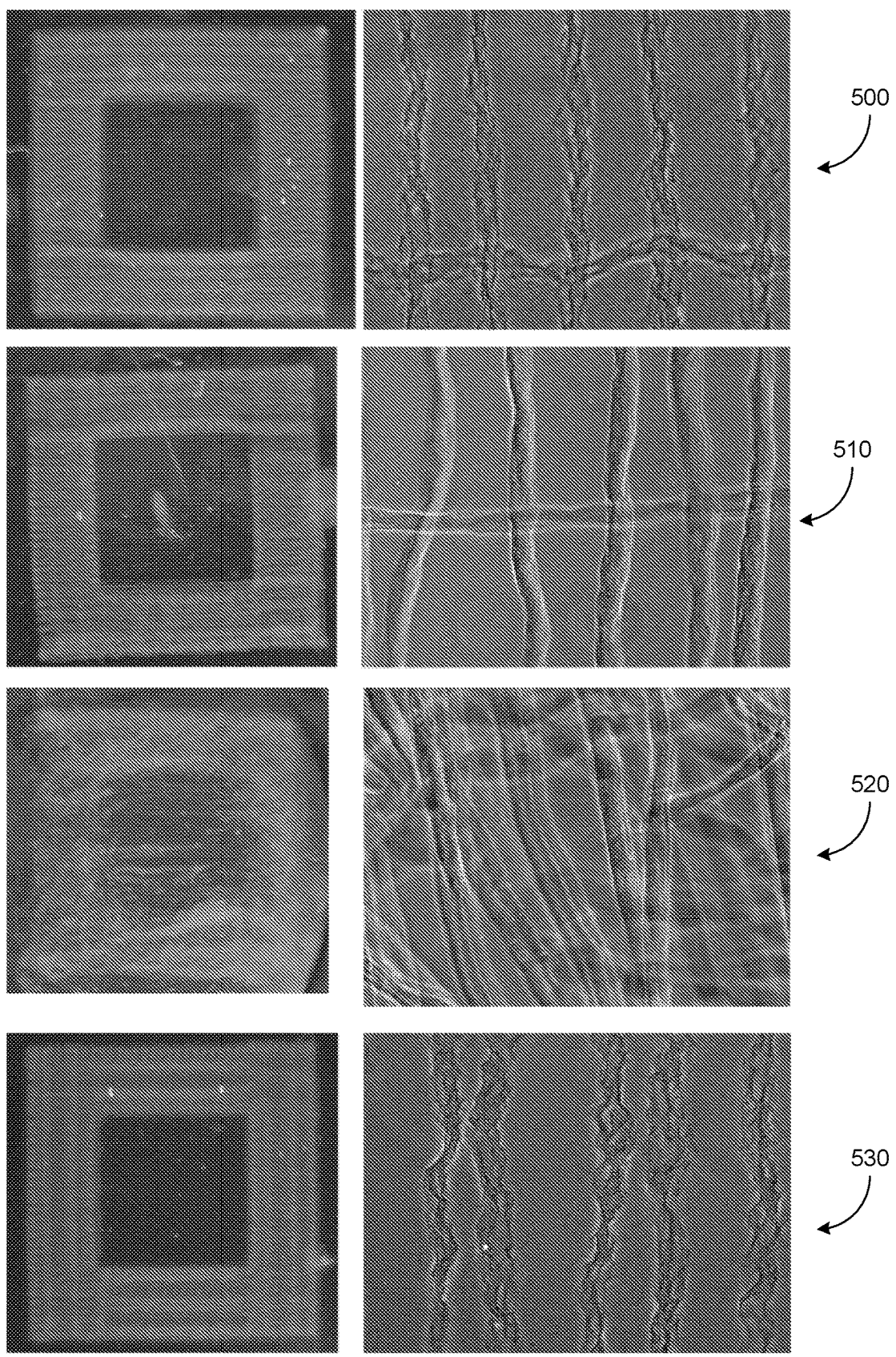
Figure 5B:
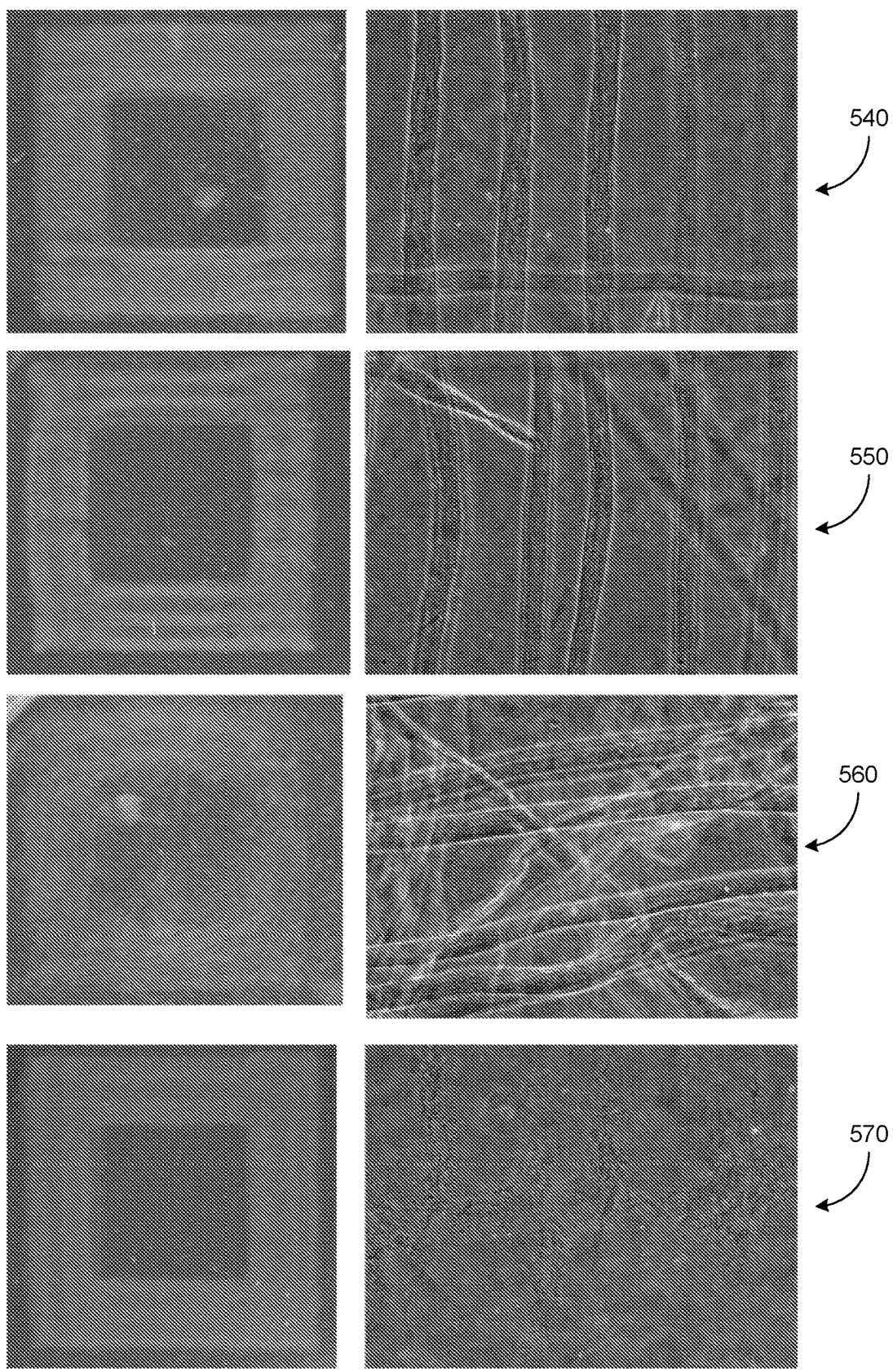

FIGS. 5A-5B show example printed strands 500-570 that are printed in different support materials. The left image for the strands includes a zoomed out image, while the right image is magnified. Strands 500-530 include Fisher Gel B pH 6, 0% gum arabic. Strands 540-570 include Fisher Gel B pH 6, 1% gum arabic. Strands 500 and 540 are printed in a support material including MW pH 7.4 at 21° C. and are shown immediately after being printed. Strands 510 and 550 are printed in a support material including MW pH 7.4 at 21° C. and are shown four hours after being printed. Strands 520 and 560 are printed in a support material including MW pH 5.85 at 21° C. and are shown four hours after being printed. Strands 530 and 570 are printed in a support material including MW pH 7.4 at 4° C. and are shown four hours after being printed. The printed strands in the MW pH 7.4 deteriorate after sitting at 21° C. for 4 hours. The MW pH 5.85 melts faster than MW pH 7.4, and results in a slurry that cannot be used for printing. HEPES/CaCl$_2$ slurry does not degrade at room temperature. HEPES/CaCl$_2$ melts noticeably slower (second melt cycle) than other support materials. The high NaCl concentration contributes to slurry degradation because the printed gel and melt point, ionic strength, and solubility are changed. Addition of NaCl affects collagen strand morphology significantly, and shows that slurry rheology determines initial collagen strand morphology, and that completion of collagen polymerization determines final strand and construct fidelity. The support material (e.g., slurry) rheology parameters include packing, particle-particle interactions through charges, slurry flow, mixing, and fracking. The parameters for printed material (e.g., collagen) polymerization include pH, ionic strength, temperature, and time.

Figure 6:
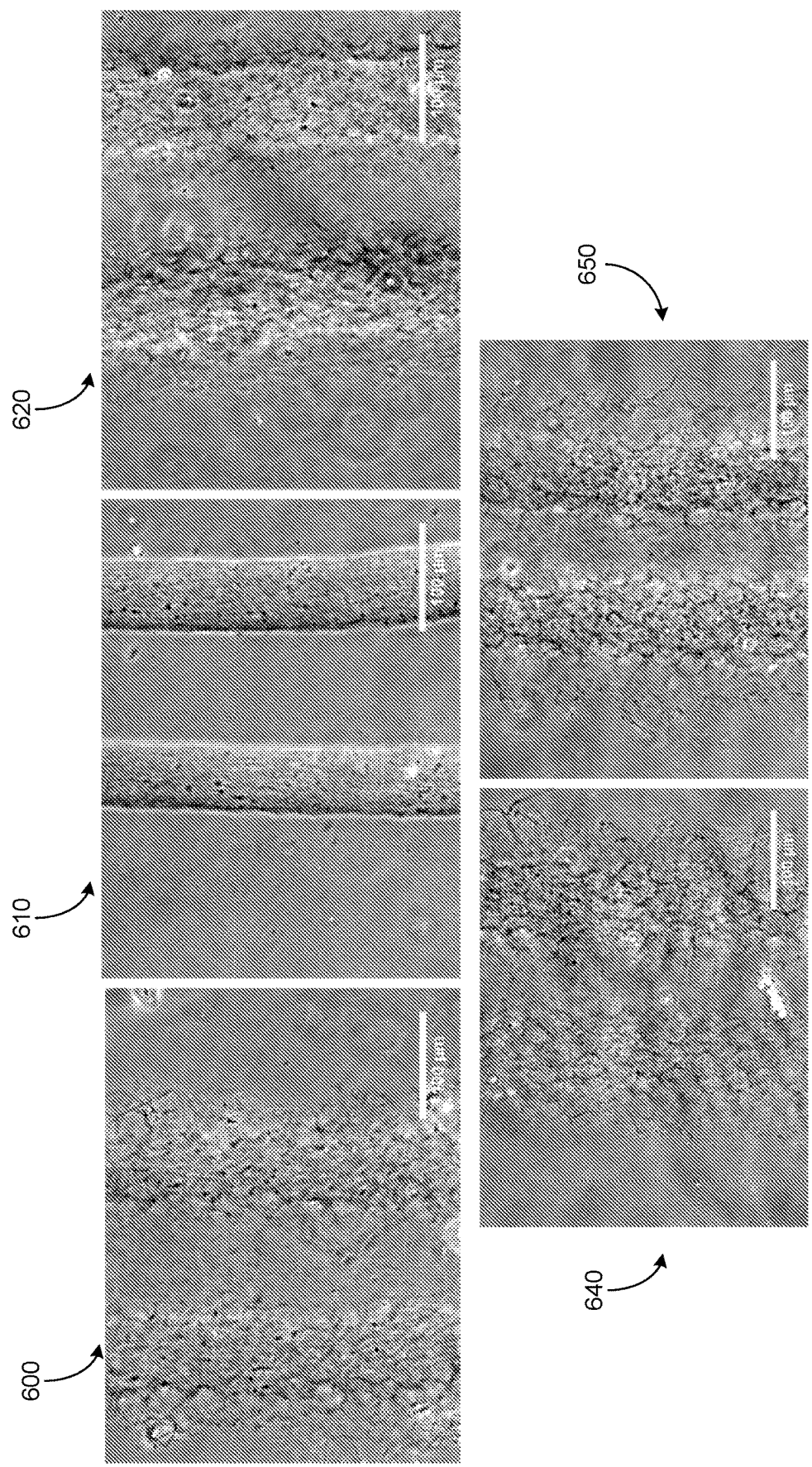

FIG. 6 shows gel B-GA (Acros) liquid phase effects on strand polymerization. Strands 600 are printed in a support material including 1×PBS. Strands 610 are printed in a support material including 10×PBS. Strands 620 are printed in a support material including 200 nM HEPES. Strands 630 are printed in a support material including Essential 8 medium. Strands 640 are printed in a support material including an extracellular buffer.

Figure 7:
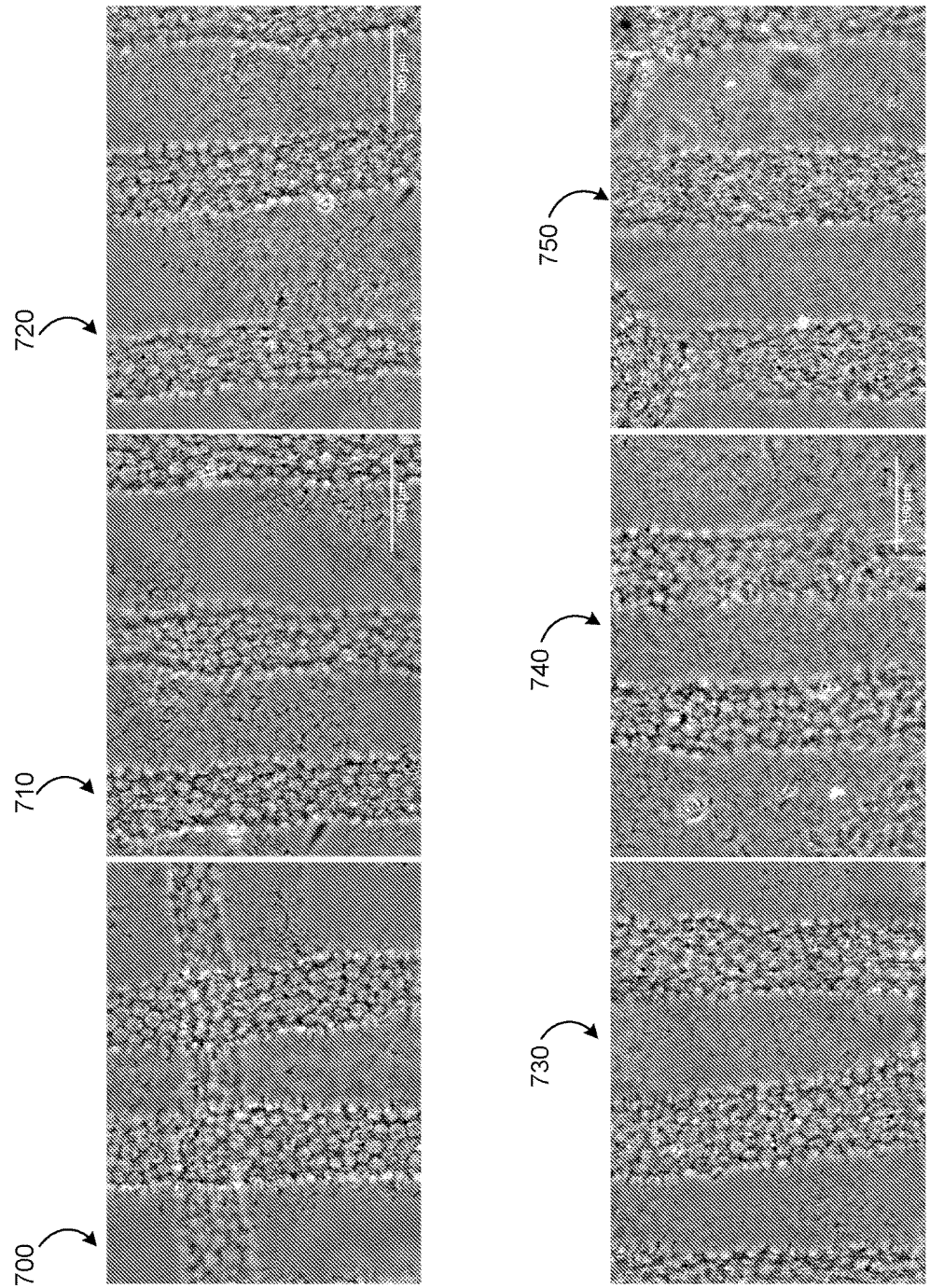

FIG. 7 shows effects of altering pH on strand polymerization. Each image depicts strands 24 hours after printing. Strands 700 are printed in a support material including a buffering agent with a pH of 8.5. Strands 710 are printed in a support material including a buffering agent with a pH of 9. Strands 720 are printed in a support material including a buffering agent with a pH of 9.5. Strands 730 are printed in a support material including a buffering agent with a pH of 10. Strands 740 are printed in a support material including a buffering agent with a pH of 10.5. Strands 750 are printed in a support material including a buffering agent with a pH of 11.

Figure 8:
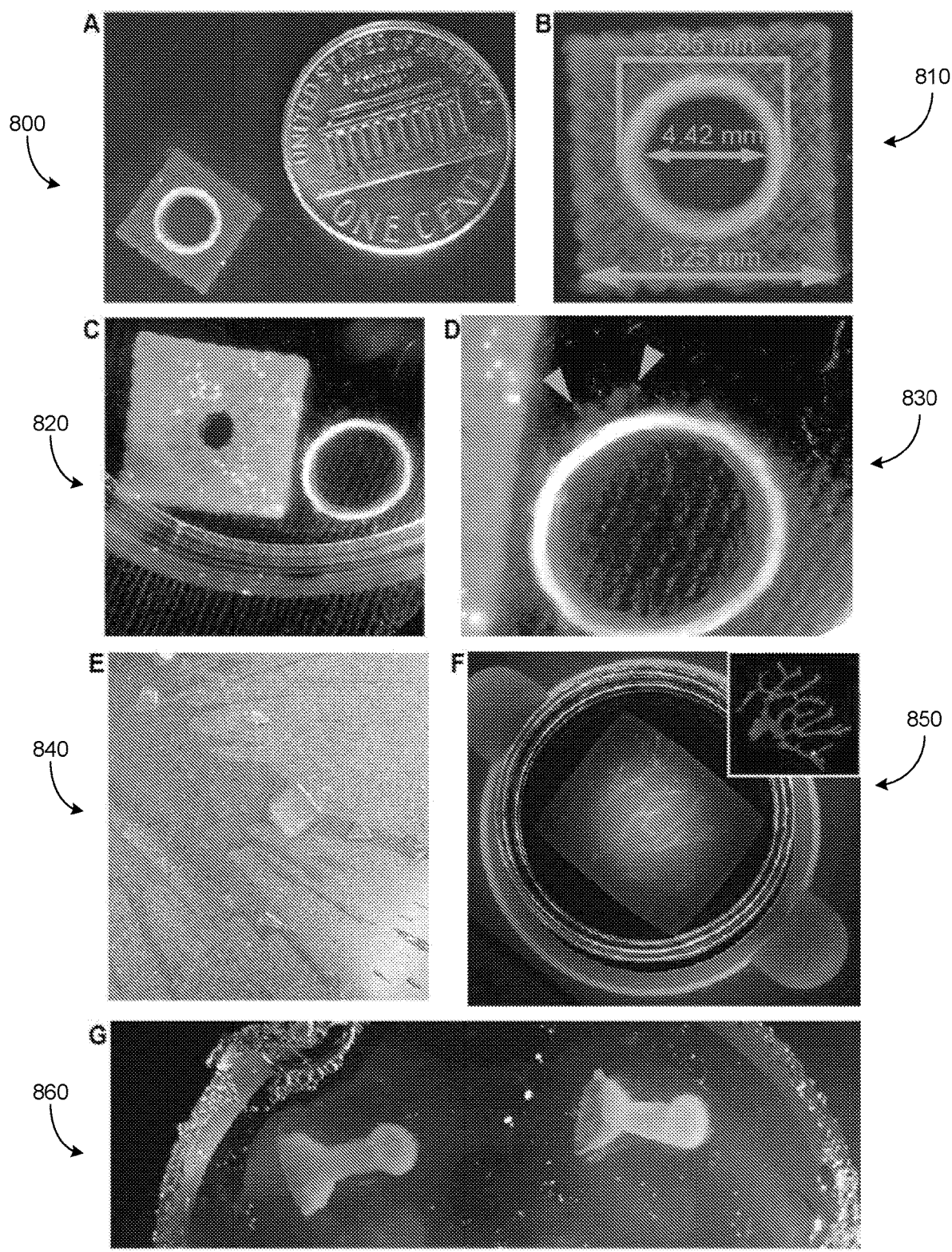
FIG. 8 shows an example of multi-material embedded printing.

FIG. 8 shows examples of multi-ink printing. As described above, collagen and other slow-gelling inks are prone to diffusion in the slurry. This phenomenon is visible as a diffuse haze surrounding collagen FRESH prints, and the only current solution to this is more aggressive methods of gelation in the print bath. Efforts to curb this diffusion include the use of NaOH, Proton Sponge (Sigma), and post-treatment crosslinking chemicals such as riboflavin, transglutaminase, and glutaraldehyde.

In some implementations, rings of collagen printed without a reinforcement such as a surrounding gel are not handleable. Most unmodified collagen hydrogel 3D prints cannot be lifted out of solution without introducing permanent deformation, and this is because the collagen hydrogel is too weak to support itself outside of solution. Including a rigid hydrogel such as alginate alongside the collagen would provide a reinforcement that would fuse to and sustain the collagen's geometry out of solution.

A ring of printed collagen hydrogel 800 supported by a printed alginate mesh was shown to not only remained fused at the border of the two hydrogels but also maintain correct dimensions even after being transported in air multiple times. The multi-material print 800 shows an inner ring of collagen hydrogel surrounded by alginate hydrogel stained with Alcian Blue, with a U.S. penny for scale. The largest dimensional deviation from the file was found at the sides of the alginate mesh, which were supposed to be 8 mm but turned out closer to 8.25 mm. The collagen ring was supposed to have an internal diameter of 4.4 mm and an outer diameter of 6 mm. The measurements 810 for the edge of the alginate mesh and the internal and external diameters of the collagen ring are shown. The measured construct 810 shows dimensions consistent with the intended diameters. In another example, collagen sections 830, which were manually plucked from their alginate mesh counterparts 820, brought with them portions of alginate mesh during dissection. The dissected multi-material print 820 shows a collagen ring on the right and alginate mesh on the left. The fusion between the alginate and collagen portions of these multi-material prints is thought to be responsible for maintaining collagen geometry during handling. Furthermore, a multi-material collagen and alginate print of a scaled-up developing mammary duct epithelium survived a drop to the lab floor. The multi-material print 840 is shown on the floor of a lab after having fallen several feet along with shards of its parent beaker. After it was recovered and imaged, it was shown to be intact and encased in alginate fibers. The removed collagen ring 850 shows alginate fibers that were fused to the collagen and could not be separated, proving fusion of the gels. The print 840 was recovered and is shown under dark field illumination, showing maintenance of the fragile collagen component 850 inside the print's interior. Inset is the file for the collagen component.

Since collagen by itself is a fragile material incapable of being delicately printed in a manner that bears its weight outside of solution, this method of reinforcing collagen with alginate is a solution for creating and allowing the manipulation of complex collagen components. The collagen can be isolated from the alginate without damage by submersion in a calcium-chelating bath, which results in dissolution of the alginate mesh and complete release of the collagen component 860. The collagen-based 3D printed tissues 860 are removed from alginate threads. These constructs displayed the compaction of collagen constructs when seeded with cells, while maintaining overall geometric fidelity. Due to the presence of the alginate mesh, it is noted that these constructs could be easily handled, seeded, cultured, and fixed without every touching or interfering with the collagen component.

In comparison to other techniques utilizing fluid inks, FRESH is faster, capable of printing more materials, and it can do so while allowing for complete release of a print from an embedding medium. Table 3.2 shown below summarizes the differences.

FIG. 9 shows a comparison of FRESH to other fluid printing techniques. Direct write printing is representative of FDM of fluids and many other techniques.

Example Structures

Being able to fabricate any geometry from combinations of unmodified ECM allows design tissues with architecture that mimics in vivo conditions. The FRESH technique was used for additive manufacturing of a set of complex biomimetic multi-material hydrogel scaffolds suited for tissue culture.

A collagen hydrogel containing cells may compact over time due to the adhesion, proliferation, and remodeling of the cells. If this process is unregulated, many constructs will compact to a dense state containing a necrotic core. Many engineered tissues consist of a cellular gel that is compacted around a mandrel or series of rigid posts meant to align internal cells based on the stresses inside the gel. In an unconstrained tubular construct, compaction would manifest as initial closure of the internal lumen and eventual fusion into a dense mass. It is therefore reasonable to expect an engineered branching construct such as a ductal epithelium to compact into a denser, dysfunctional state with necrotic regions and partial lumen closure. While it may be possible to formulate a collagenous, cellular hydrogel ink that does not compact in culture, the requirements for this are likely beyond the scope of this project. Instead, it should be easier to embed the collagen construct inside a sparse net of rigid alginate hydrogel extrusions.

Figure 10:
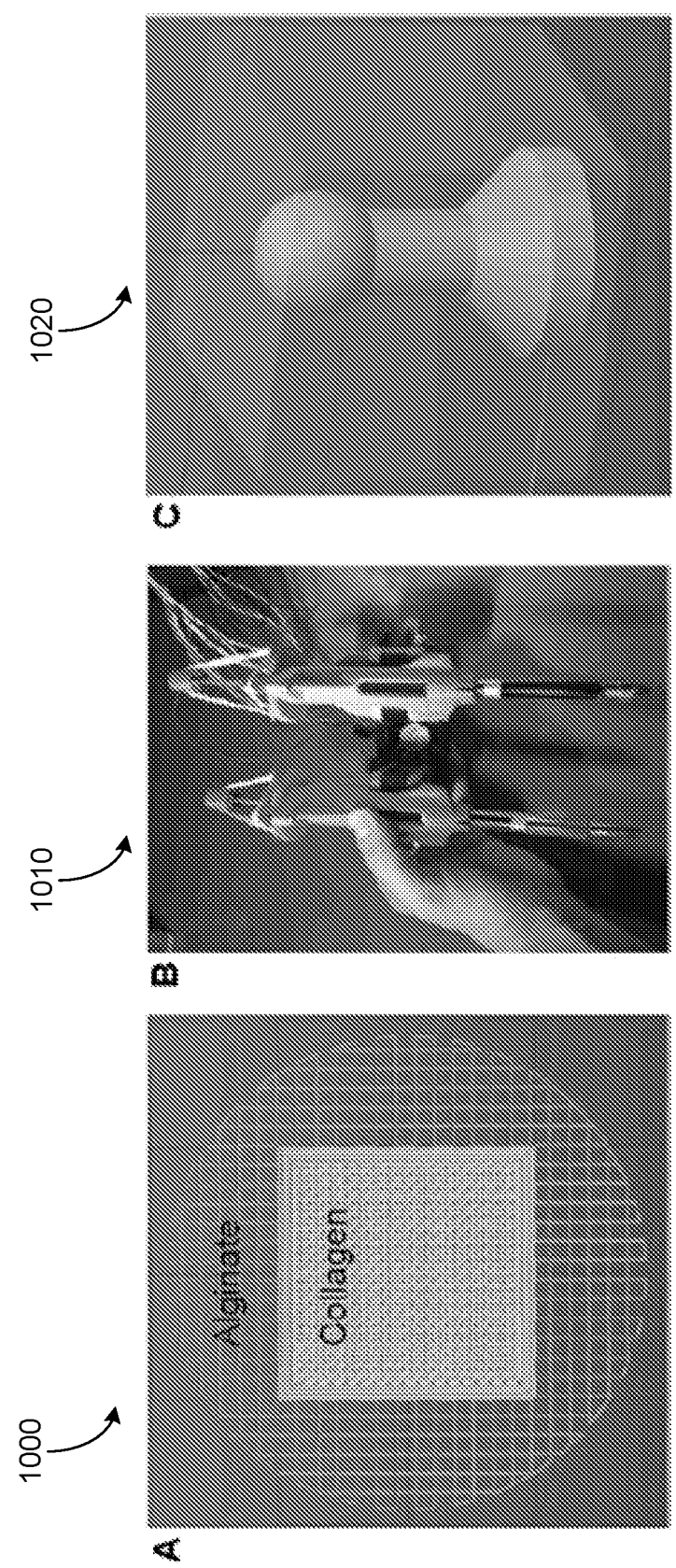
FIGS. 10-11 show examples of multi-material prints.

FIG. 10 shows a multi-material print process that uses an alginate scaffold over collagen, shown by print 1000. A soft collagen hydrogel mass is 3D printed alongside a sparse net of a more rigid alginate hydrogel. Forces that normally deform the collagen hydrogel would instead be forced to work against the alginate mesh that surrounds the construct. The alginate would be included in the print as a separate ink in an additional extruder, and the mesh would be generated as a sparse infill pattern normally seen in the interior of 3D prints. Dual-extrusion of collagenous hydrogel and alginate ink relies on a dual extruder 1010. Testing this approach of immobilizing one printed material within another would likely require a simplified geometry such as a vertical tube of collagen gel to be printed in alginate mesh 1020. Two steppers power a pair of syringe pump extruders with collagen and alginate hydrogel inks. Measuring the dimensions of the tube is accomplished as with the gauging of print accuracy using calibration prints—micrographs are compared with known digital dimensions. A hollow tube is printed from a soft hydrogel inside an alginate mesh to preserve its shape during handling or culture.

Replicating the in vivo environment in vitro means engineering constructs to closely mimic the appearance of in vivo equivalents. Imaging data can be processed from optical projection tomography (OPT) of whole-mount tissue samples, and, through software analysis, model the tissue as a 3D printable solid. Printing an entire ductal epithelium modeled from imaging data ensures that the internal features of the epithelium such as the bifurcations within the branching tree are geometrically representative of native tissues.

Since it has been found that ductal epithelium possesses four distinct developmental morphologies which are intimately associated with the three most commonly used mouse strains in breast cancer research, it is important to be able to vary the chosen geometry of the epithelium and obtain similar levels of accuracy across different morphologies. Verifying said accuracy of the 3D prints involves imaging them using a technique such as OPT or confocal microscopy, for the data obtained from such processes can be used to directly compare the output of the 3D printer with the input file's dimensions. 3D printing an accurate model of the ductal epithelium to culture epithelium will allow researchers to closely simulate the in vivo environment for DCIS and potentially even study the in situ-to-invasive transition without using a host organism. The opportunity to probe the behavior of DCIS in an environment that is both biomimetic and entirely customizable would prove an invaluable tool for understanding which instances of DCIS deserve intervention. Indeed, the printed epithelial model can be generated from imaging data for a specific patient with DCIS, and then a coring needle biopsy could be used to seed the construct with both the patient's epithelial cells and the suspect lesion. Growing the lesion outside the patient would allow doctors to identify necessary treatment routines and targeted therapies without assuming the worst-case pre-malignant scenario, which is a prevalent assumption among current patients.

The flexibility of the multi-print application described above is such that it allows anyone to prototype delicate branching structures out of any soft hydrogel, with or without cells and without the fear of cells compacting away any complex geometry.

The print was modeled in 3D printing software. The collagen component for a given model was imported into the software, and, then, the accompanying alginate component was imported as a "part" of the original collagen component by utilizing the software mesh-editing menu. The collagen component was specified as using the first extruder and the alginate component the second. The alginate component was then assigned setting modifiers shown in Table 1 below.

TABLE 1

Collagen and Alginate Properties for Example Print

| Variable Name | Value for Collagen | Value for Alginate |
| --- | --- | --- |
| Extrusion width | 0.08 mm | 0.15 mm |
| Infill % | 100% | 40% |
| Perimeters | 3 | 0 |
| Speed of Infill | 5 mm/s | 23 mm/s |
| Infill Perimeter Overlap | 0% | 55% |
| Infill Pattern | Concentric & Rectilinear | Rectilinear |

To print two materials, the first and second Replistruders in the duet printer were loaded with a 100 μL syringe of collagen featuring an 80 μm needle and a 2.5 mL syringe of alginate featuring a 150 μm needle. The 80 μm needle on the collagen syringe was so long and thin that it was subject to deflection during printing, resulting in poor rendering of machine movements by the extruder. Any vertical tubes printed by this needle ended up fused shut, and sharp corners were rounded. The solution to this was to laser-cut a larger needle to use as a brace. A ½ in long 250 μm needle was laser cut, filled with uncured epoxy, slid onto the 80 μm needle, and baked at 65° C. for 2 hours.

MK2's were thoroughly washed in warm 70 mM $CaCl_2$ with 25 mM Na-HEPES for at least 24 hours before submersion into 70 mM $CaCl_2$ with 25 mM Na-HEPES and 50% v/v Ethanol. MK2's in this 50% Ethanol solution were then allowed to sit for 24 hours at 4° C. On the day of seeding and initiating culture, constructs were removed from this ethanol solution and placed into warm 70 mM $CaCl_2$ with 25 mM Na-HEPES. After resting in this fluid for at least 30 minutes, the constructs were washed with fresh 70 mM $CaCl_2$) with 25 mM Na-HEPES before being placed into cell media supplemented with 10 mM $CaCl_2$).

ATCC MCF7 (HTB-22) and ATCC MCF 10A (CRL-10317) cells were transfected with pHIV-ZSGreen lentivirus and flow sorted to select for transfected cells. Resulting cells were cultured per ATCC guidelines. Constructs were washed in sterile-filtered 20° C. 1% $CaCl_2$) with 25 mM Na-HEPES. Constructs were then soaked in 20° C. sterile-filtered ATCC media, supplemented with 10 mM $CaCl_2$) and 200 μg/mL Penicillin-Streptomycin for 10 minutes. Then constructs were placed in a 6-well plate with one construct per well. Supplemented media was added to each well until half of the construct was submerged (approx. 3 mL). Cells were suspended in supplemented media at $1 \times 10^6$ cells/mL. 50 μL of cells suspension was pipetted directly into the center of the funnel portion of each construct. For half of the constructs, they were turned onto one of their 4 sides and allowed to rest there for 20 minutes at 37° C. Then, the seeding was repeated followed by 4 more resting periods until each construct was seeded on each side. Constructs were quickly imaged on an Olympus IX83 fluorescence microscope to ensure cells were in the constructs. One construct of the three for each cell type that was not rotated during seeding was seeded with 200,000 cells in the upright position. All constructs were finally returned to their upright conditions and placed in 37° C. culture for 7 days, with regular media exchange. After 7 days, media was aspirated from each well before fixation.

Cultured MK2's were rinsed with 1×PBS (supplemented with 0.625 mM MgCl2 and 10 mM $CaCl_2$)) at 37° C., fixed in 4% w/v formaldehyde with 10 mM $CaCl_2$ (Polysciences, Inc.) for 15 min, and then washed 3 times in 11 mM $CaCl_2$) with 25 mM Na-HEPES. The fixed MK2 was imaged with a Nikon AZ-C2 macro confocal microscope with a 5× objective (0.45 NA) and a Leica SP5 multiphoton microscope with a 10× (NA=0.4) objective and a 25× (NA=0.95) water immersion objective. 3D image stacks were deconvolved with AutoQuant X3 and processed with Imaris 7.5.

In cases where the collagen and cells were obscured by alginate threads, it was possible to remove the alginate by washing a fixed MK2 in a 100 mM Na-Citrate buffer solution for 12 hours. Then, the construct could be embedded in 10% w/v Gelatin A and sectioned. The resulting collagen component with attached interior cells was then accessible by the microscopes. After removal of alginate threads, 3D z-stacks were acquired using reflectance imaging of collagen I at 435 nm with a Leica SP5 multiphoton microscope and a 25× water objective (NA=0.95). The thickness of the collagen I hydrogels in cross-section was measured.

Figure 11:
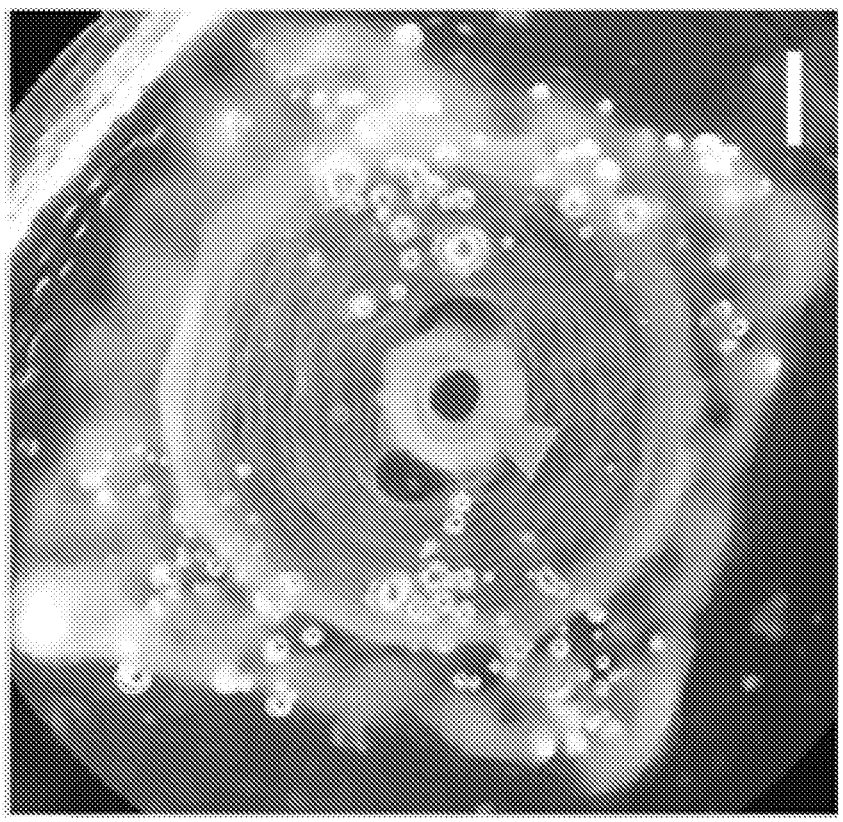

After the collagen extruder's needle was reinforced, MK2 constructs created in a coacervate slurry possessed perfectly concentric circular extrusions of collagen, with little to no deflection or lagging of the extrusion visible. FIG. 11 shows the output print 1100. This quality of output is largely attributable to both the extra-fine texture of the coacervate, which has monodisperse, microscopic particles and the attention paid to alignment of separate extruder needles pre-print. The exterior of MK1 and MK2 constructs possessed a square profile with the 90° crosshatch pattern of alginate mesh. The rim of the funnel nearly always possessed a diameter within 1% of the intended value. Initial data shows that the internal diameter of the duct falls within approximately 2% of its intended value. The same data indicates that when the prints were released, post-culture, they were found to possess buds that were always within 2% of the intended diameter of the file used to print them.

Figure 12:
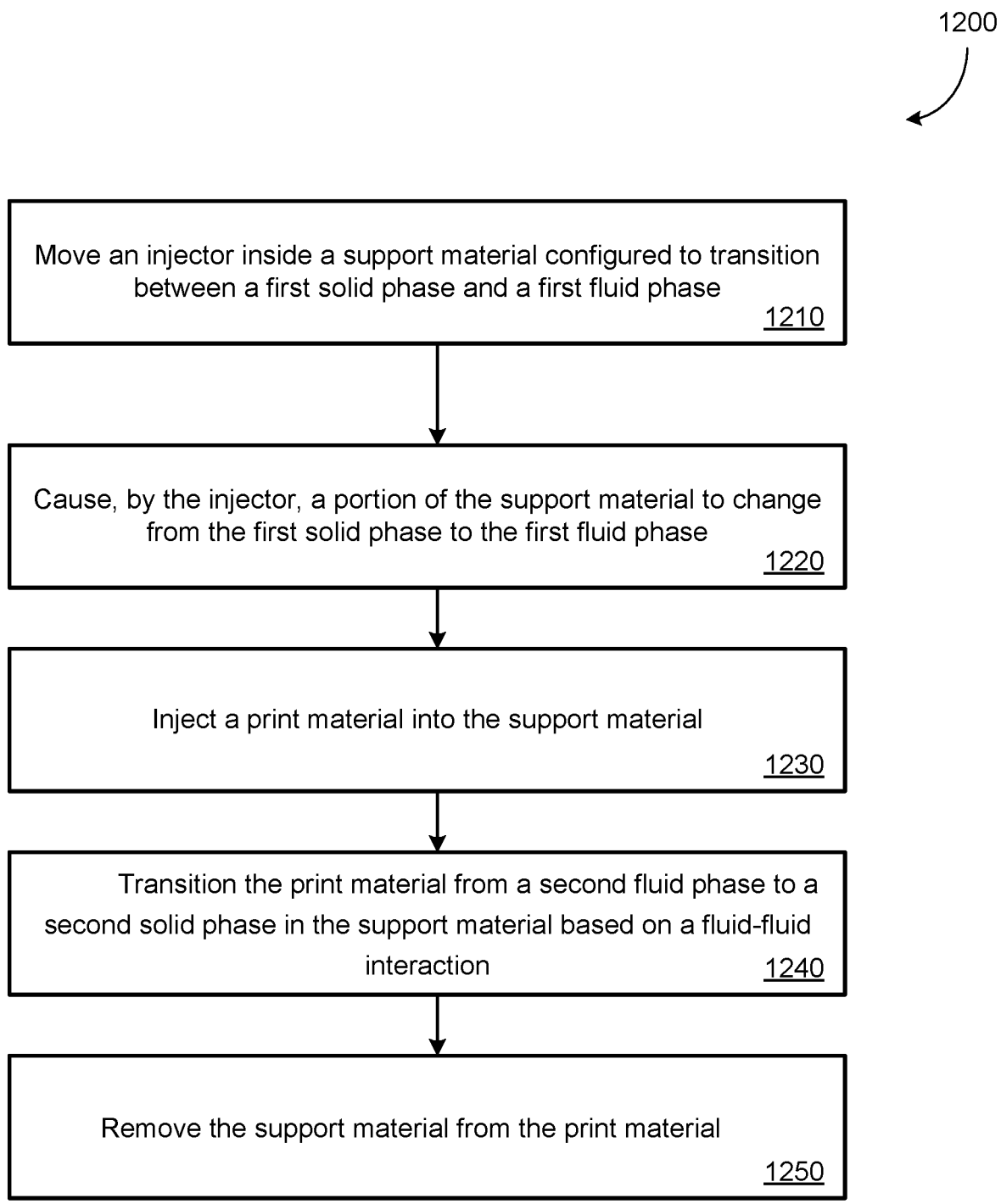
FIG. 12 shows a flow diagram for an example embedded printing process.

FIG. 12 shows a flow diagram 1200 of an example embedded printing process. An injector is moved (1210) inside a support material configured to transition between a first solid phase and a first fluid phase. The injector causes (1220) a portion of the support material to change from the first solid phase to the first fluid phase. The injector injects (1230) a print material into the support material. The print material transitions (1240) from a second fluid phase to a second solid phase in the support material based on a fluid-fluid interaction between the first fluid phase of the support material and the second fluid phase of the print material. The support material is removed (1250) from the print material.

A number of embodiments have been described. Nevertheless, it will be understood that various modifications may be made without departing from the spirit and scope of the claims. Accordingly, other embodiments are within the scope of the following claims.

What is claimed is:

1. A system comprising:
    a support material comprising a first solid phase and a first fluid phase, the support material being configured to flow in response to experiencing a mechanical stress; and
    a print material embedded within the support material, the print material configured to transition from a second fluid phase to a second solid phase within the support material by a fluid-fluid interaction between the first fluid phase of the support material and the second fluid phase of the print material;
    a buffering material having a predetermined concentration within the support material, the buffering material causing the transition of the print material from the second fluid phase to the second solid phase within the support material at a predetermined rate based on the predetermined concentration.

2. The system of claim 1, wherein the support material is more basic than the print material, and wherein the print material is acidic, and wherein a transition of the support material comprises a neutralization of the print material during the fluid-fluid interaction of the print material and the support material.

3. The system of claim 1, wherein the print material comprises at least one of collagen, gelatin, and alginate.

4. The system of claim 1, wherein the print material comprises a strand including a diameter between about 10-250 micrometers.

5. The system of claim 1, wherein the print material is a first print material, and wherein the system comprises a second print material that forms a mesh that encases the first print material, the mesh configured to support a geometry of the first print material when the support material is removed from the first print material.

6. The system of claim 5, wherein the first print material comprises collagen, wherein the second print material comprises alginate, and wherein the support material comprises calcium.

7. The system of claim 1, wherein the support material comprises a salt concentration that is configured to induce a gelation of the print material from the second fluid phase to the second solid phase in the support material.

8. The system of claim 7, wherein the salt concentration of the support material is approximately 40 g/L-80 g/L.

9. The system of claim 1, wherein the support material comprises a coacervate slurry.

* * * * *